United States Patent [19]
Liprie

[11] Patent Number: 5,395,300
[45] Date of Patent: Mar. 7, 1995

[54] HIGH DOSAGE RADIOACTIVE SOURCE

[75] Inventor: Sam F. Liprie, Lake Charles, La.

[73] Assignee: Omnitron International, Inc., Houston, Tex.

[21] Appl. No.: 712,343

[22] Filed: Jun. 7, 1991

[51] Int. Cl.⁶ .............................................. A61N 5/00
[52] U.S. Cl. ......................................... 600/3; 376/158
[58] Field of Search .............................. 600/1, 3, 6–8; 128/897–899; 424/1.1; 427/2, 5

[56] References Cited

U.S. PATENT DOCUMENTS

| | | | |
|---|---|---|---|
| 4,702,228 | 10/1987 | Russel, Jr. et al. | 600/8 |
| 4,815,449 | 3/1989 | Horowitz | 600/8 |
| 4,861,520 | 8/1989 | van't Hooft et al. | 600/8 |
| 5,084,002 | 1/1992 | Liprie | 600/7 |

FOREIGN PATENT DOCUMENTS 830573 12/1969 Canada .................................. 600/8

Primary Examiner—William E. Kamm
Assistant Examiner—J. P. Lacyk
Attorney, Agent, or Firm—O'Conner, Cavanagh

[57] ABSTRACT

A method of fabricating a radioactive core to be integrated within a source wire for use in radiation treatment of tumors within the body of a patient utilizes a thin elongate fiber of substantially pure iridium encapsulated in a straight quartz tube substantially transparent to the flux of a beam of radiation. The iridium fiber is oriented lengthwise along the axis of the tube, so that the fiber is restrained from curling. The tube and the fiber therein are irradiated with a beam directed normal to the axis of the tube while rotating the tube about the axis, to render the fiber radioactive to a predetermined level of activity. The method is adapted to produce a generally cylindrical Ir-192 source having a longitudinal axis of symmetry, a length of about one centimeter, a diameter of about 0.35 millimeter, a weight of about 20 milligrams and a radioactivity level of at least approximately 10 curies.

12 Claims, 1 Drawing Sheet

HIGH DOSAGE RADIOACTIVE SOURCE

BACKGROUND OF THE INVENTION

The present invention relates generally to radioactive sources used in the treatment of cancerous tissue. More particularly, the invention resides in apparatus, and methods for producing apparatus, incorporating a high dose radioactive source to be delivered into the body of a cancer patient for relatively short term but repeated exposure of a malignant tumor to localized in vivo radiation from within. The delivery may be through a catheter which terminates at or beyond the tumor site.

The type of radiation treatment of malignant tumors most often performed involves directing a beam of radiation from a point external to the patient's body onto the area of the body in which the tumor is located, for the purpose of shrinking and ultimately destroying the tumor. Such treatment is not particularly selective except in a somewhat gross sense, and therefore exposes healthy tissue to the high dosage of radiation in the beam and consequent potential injury. Another technique for radiation treatment, known as brachytherapy, attacks tumors from within the body. The brachytherapy method generally employs a highly radioactive source integral with a guidewire (the entire unit being referred to herein as a source wire) which is typically delivered via a catheter (although it may be delivered through a natural cavity, duct or vessel of the body) directly to the tumor site for localized irradiation. The latter technique is less likely to expose healthy tissue to injury than if external beam radiation were used. One or more catheters, for example, are implanted in the patient's body to provide a path from an external point to and through the tumor site, so that the interior of the tumor mass is accessible via the catheter(s). The radioactive source, with the typical dose available in the prior art being up to a range of eight or nine curies, is then mechanically delivered on the retractable guidewire through the catheter for localized irradiation of the tumor for a very short period of time, usually in the range of only seconds up to a few minutes per treatment.

The high dose source is secured to the tip of the guidewire, the other end of which is attached to a controllable apparatus known as a remote afterloader, for advancement or retraction. Advancement of the source wire through the catheter to the proper location for treatment of the tumor is achieved by calibration according to the measured distance traveled by a previously advanced and retracted dummy wire having an opaque tip marker for fluoroscopic observation. The source wire is left in the selected position for a predetermined time interval (programmed into the afterloader) deemed necessary to provide the desired treatment, and is then automatically retracted and returned to a shielded storage area within the afterloader.

The treatment regime is usually repeated at regular short intervals over a period of many days, weeks or months until the tumor has been completely eliminated or at least shrunk to the maximum practicable extent. Among the advantages of this type of radiation therapy are exposure of the tumor to fractionated treatment doses of localized radiation so that each individual treatment need only be of extremely short duration to provide the desired effect while reducing the extent of patient discomfort, and to provide more rapid shrinking of the tumor while avoiding prolonged exposure of healthy tissue to radiation.

Because this type of therapy is more applicable to inoperable malignancies deep within the body, the site of the tumor(s) is usually difficult to reach as the source wire is guided through the path provided by the implanted catheter. It is often the case that this path is long, narrow and tortuous with numerous sharp turns. It is essential, therefore, that the source wire should be extremely thin and flexible. This means it is necessary that the radioactive source, the core, must be sufficiently small to traverse the path to and from the tumor, and yet, be capable of delivering a radiation dosage at least as high and, desirably, even higher than that available in the highest dosage prior art devices, namely, up to ten curies.

One material frequently used for hot (radioactive) cores capable of delivering high dosage radiation to the tumor site by means of a remote afterloader is substantially pure iridium, which can be irradiated to a relatively high level of radioactivity as Ir-192, in a relatively small size. Ir-192 has been produced by prior art techniques in a nuclear reactor with dosages of up to 10 curies in a diameter small enough to allow a source wire diameter of about 1.1 millimeters (mm). Other conventional source materials include cobalt, cesium, palladium, gold, and iodine.

The foremost technique employed in the prior art for fabricating source wires starts with building the radioactive core by first stacking a plurality of small irradiated disks and then pinning them together through their common central hole. Unfortunately, this approach has not been successful in producing a sufficiently high dose radioactive core in a package size suitable for fabricating a source wire thin enough to traverse the smallest catheters of interest for interstitial and/or intraluminal brachytherapy. Moreover, the disks can be difficult to handle, and present a serious contamination problem if, during assembly or upon breakage of the source wire, they should spill out of their pinned or otherwise contained configuration.

It is a principal object of the present invention to provide a new and improved radioactive source or core for in vivo localized radioactive treatment of malignant tumors, and which can be produced with radioactivity levels of at least 10 curies in a smaller package than has heretofore been attainable.

It is another important object of the present invention to provide an improved design and method of fabrication for a high dose radioactive source for use in interstitial, intraluminal and/or intracavitary brachytherapy.

SUMMARY OF THE INVENTION

According to one important aspect of the present invention, a new and improved radioactive source is provided for use in shrinking and destroying malignant tumors within a patient's body by localized in vivo radiation thereof. The source or core, preferably iridium, is fabricated by a method which enables it to be irradiated to a radioactivity level of at least about 10 curies in a sufficiently small package to produce an ultra-thin Ir-192 source wire with a diameter in the range from about 0.6 to 0.7 millimeter (mm). In the preferred embodiment, the radioactive source is a substantially pure iridium (Ir-192) fiber core approximately one centimeter (cm) in length and about 0.35 mm in diameter.

In the method of the invention, 20 to 21 milligrams (mg) of iridium are packed into a containment vessel, preferably a substantially pure quartz vial, in a one cm long axially oriented configuration to provide maximum surface area for contacting the neutron beam or beams imparted in a nuclear reactor. If a wider quartz vial were used to encapsulate the iridium fiber, the fiber could undergo bending and curling, because the impinging neutrons create heat. When the fiber curls, self-shielding occurs; that is, the fiber configuration itself prevents the incoming nuclear radiation from reaching the interior of the core. Another problem encountered in the irradiation part of the process if a thick glass (quartz) container were used, is that the glass wall itself will attenuate much of the neutron beam, to prevent the radiation dosage from reaching the desired level of activity. The prior art manufacturing techniques for producing cores to be used in smaller sized source wires have generally been capable of producing core radioactivity levels of only up to about 9 curies.

In the method of the present invention, the quartz tube containing the core is rotated about its axis of symmetry within an aluminum canister. The entire structure is housed in a nuclear reactor, so that the neutron beam penetrates the canister and bombards the quartz tube, and hence the iridium fiber, on all sides. This assures contact of the beam with maximum surface area of the fiber. Nevertheless, if the fiber were thick and short, the beam would not penetrate fully into the interior of the fiber. Similarly, the wall thickness of the quartz vial affects the amount of radiation that reaches the fiber. The thicker the wall, the greater the fiber shielding and beam attenuation, which is undesirable. Currently, the most powerful commercial nuclear reactor available can produce a neutron beam capable of irradiating a material such as iridium to a maximum of 500 to 550 curies per gram of the material. Thus, the maximum attainable radioactivity that may be imparted to a 20 mg fiber of iridium is 10 to 11 curies.

The substantially pure quartz vial into which the core is placed is virtually transparent to nuclear radiation, in part because of the nature of the material itself and also because of its thin walled configuration. The vial or tube has a very small inner diameter, which assures retention of the iridium fiber core in an essentially axial orientation and precludes contamination and flaking off of the vessel onto the core. The quartz vial is vacuum sealed because the impinging neutrons can cause sufficient pressure and heat buildup to produce an explosion if oxygen were present in the vial. In addition, heat and the neutron bombardment cause the core to become brittle. If the quartz vial were overly thick, considerable heat would need to be applied to obtain a vacuum seal prior to irradiation. In those circumstances, after the vial is withdrawn from the reactor the core may crumble when it is removed from the vial. To alleviate the situation, the method of the invention utilizes a heat sink and a very thin quartz vial to transfer, remove and reduce the quantity of heat delivered during the vacuum sealing portion of the process.

Additionally, because the containment vessel is vacuum sealed, when the tube is scored along a plane normal to the axis (e.g., using a diamond saw) and then cleanly broken, any flakes of irradiated iridium are retained within and fall to the bottom of the tube as air rushes in to eliminate the vacuum. Thus, the radioactive contamination does not escape into the surrounding environment.

Accordingly, it is another object of the invention to provide a method of fabricating an approximately 10 curie radioactive source of considerably smaller size in at least one dimension than had heretofore been attainable, for use in practicing brachytherapy; and wherein the method is also effective to substantially prevent radioactive contaminants which are by-products of the fabrication from escaping into the surrounding environment.

SUMMARY OF THE DRAWINGS

The above and still further objects, features and attendant advantages of the present invention will become apparent from consideration of the following detailed description of certain presently preferred embodiments and methods of the invention, taken in conjunction with the accompanying drawings, in which.

Figure 1:
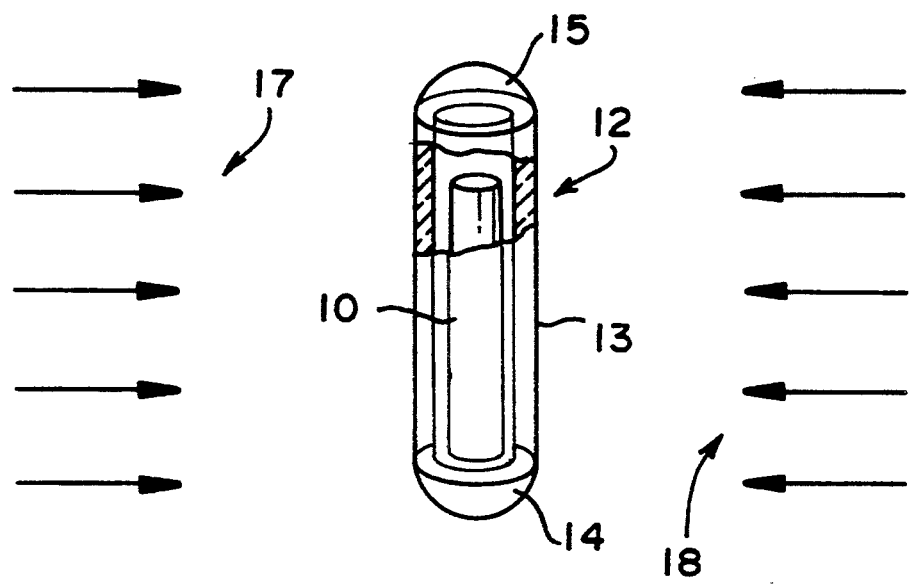
FIG. 1 is a perspective view of a presently preferred embodiment of a source in the configuration of a fiber core according to the present invention, assembled into a containment vessel for irradiation, and illustrating the direction of the impinging neutron beams.

Detailed Description of the Preferred Embodiment and Method

Prior to discussing details of the invention, it should be noted that the Figures of drawing are not to scale. For example, wall thickness and element spacing are shown to be dimensioned and to have relative dimensions to improve the clarity of the depiction, rather than to depict actual sizes, either absolute or relative. Currently, the most efficient commercial nuclear reactors, one of which is available at the University of Missouri, can deliver specific activity of 500 to 550 curies per gram of iridium. To apply this principle to the most optimal practical situations, at least approximately 20 milligrams of iridium is needed to produce 10 curies of activity. Generally, however, the current techniques for fabricating high dose radioactive sources for brachytherapy applications are incapable of attaining iridium source dosages exceeding about nine curies. One of the improvements achieved by the method of the invention is to virtually eliminate the shielding of one portion of the iridium from full exposure to the flux by another portion thereof during the irradiation step, which otherwise prevents the entire body of the irradiated source material from becoming activated.

According to one aspect of the present invention, the iridium is fabricated in a configuration to maximize the surface area thereof exposed to the neutron beam. Another aspect is to encapsulate the iridium to be irradiated in a container which is substantially free of impurities and transparent to neutron beam radiation (i.e., does not significantly attenuate the neutron beam passing therethrough). The relative absence of impurities tends to keep the core free of undesirable contaminants, and the transparency of the container avoids shielding the core from the flux. From the standpoint of reducing radioactive contamination of environmental fixtures and materials, it is important that the container material should by of a type that either (i) will not become radioactive as a result of exposure to the neutron beam(s) or (ii) has an extremely short half-life of radioactivity.

A further aspect of the method of the invention is to seal the iridium core under vacuum within the container during the encapsulation process. One function of the vacuum is to prevent transfer of heat to and consequent expansion of the container tube as the neutron beam reacts with the core during the irradiation process, which might otherwise cause the container to explode. Another important function of the vacuum is to prevent any loose, radioactive particles from the core from escaping when the container is subsequently opened, by virtue of the fact that at the moment of opening the outside air rushes into the opening to fill the vacuum.

According to the invention, then, among the factors taken into consideration to provide a method for fabricating an iridium core or source having a radioactive strength of at least ten curies in a package size suitable for use in practicing brachytherapy through traversal of particularly narrow and tortuous passages, are the composition and configuration of materials employed, heat transfer and sinking, and strength and attenuation of the neutron flux in the process.

Referring now to the drawings, a preferred embodiment of core 10 is composed of 20 to 21 mg of high purity iridium (i.e., having a virtual absence of impurities) which is compressed in a conventional manner into a cylinder-like fiber having a length of about one cm and a diameter of about 0.343 mm (FIG. 1). In preparation for irradiation with a neutron beam in a reactor, the core 10 is encapsulated in a containment vessel 12, preferably a thin walled high purity quartz tube 13 (FIG. 1). The composition and thinness of this vessel material renders the vessel virtually transparent to such a beam, which is important because of the aforementioned desire to reduce shielding and to expose maximum surface area of core 10 to the flux of the beam (shown in the drawing as lines of radiation) 17, which impinges on tube 13 at right angles thereto. The quartz tube is selected to have an extremely thin wall (for example, 0.6 mm thick), but of sufficient rigidity to maintain the virtually straight orientation of the fiber core 10 normal to the beam.

Another important reason for the use of high purity quartz as the containment vessel for the core 10 in the irradiation step is that the pure material has an extremely short half-life for radioactivity; decay to that extent takes place within a period of 11 to 14 days. The quartz vial preferably has an inner diameter of about one millimeter (mm), and an outer diameter of approximately 2.2 mm. This provides sufficient tolerance, relative to the aforementioned exemplary diameter of the fiber core 10, to assure that the core may be easily inserted into and removed from the tube 13, but will be sufficiently restrained by the tube to remain aligned along a straight axis during the irradiation process.

Absent the restraint imposed by tube 13, the length and thinness of the core would allow the core to relax and undergo curling with neutron bombardment and heat buildup. In those circumstances, the core could not be fully irradiated by the neutron beam, owing to the self-shielding of the center of the core by any portion of the core not oriented normal to the impinging beam. A shorter and thicker core would also result in considerable self-shielding of the very center of the core by the peripheral core material.

In practicing the method of the invention, after one end 14 of tube 13 is heat sealed, core 10 is inserted into the partially closed tube. The other end 15 of the tube is then heat sealed under vacuum, so that after sealing, the core is maintained in the containment vessel 12 under vacuum. The vacuum sealing process is performed using heat and heat sinks, the latter including as a principal component the thin-walled tube 12 itself, to transfer, reduce and remove the quantity of heat delivered to the iridium fiber core, which could otherwise damage the core.

The vessel with fiber core 10 inside is then placed in a conventional slotted containment cylinder in the reactor (not shown), for heat sinking and rotation about the longitudinal axis of the tube. The slotting allows a planar beam (shown in diagrammatic form at 17, 18, FIG. 2) to impinge on the full length of the core at both sides thereof. In a practical embodiment, a vacuum sealed core was irradiated in a University of Missouri reactor, using uranium and plutonium rods. The same or similar reactors are available at other locations for fabrication of sources for medical, commercial and industrial applications, as well as for pure research. When maximum saturation is reached, the irradiation process is ceased. No increase in the radioactivity level of the core can be achieved by further irradiation in the reactor after the point of maximum saturation has been attained.

Figure 2:
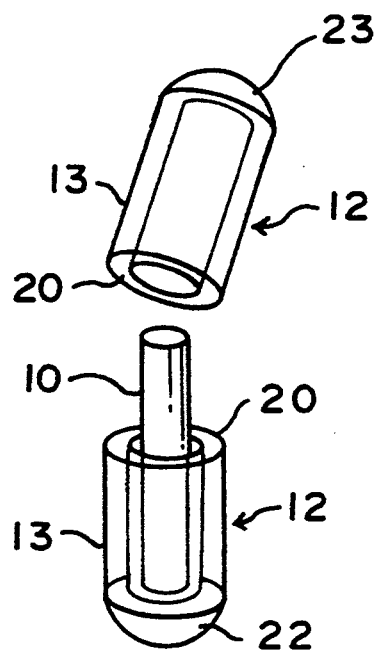
FIG. 2 is a perspective view of the containment vessel after irradiation and scoring of the vessel in preparation for removal of the now radioactive fiber core therefrom.

After the desired level of intensity (or maximum saturation) has been achieved, the vessel 13 with the encapsulated, now Ir-192, core 10 is withdrawn from the reactor. At some time thereafter (typically 11 to 14 days, to allow all impurities or contaminants to decay away) the vessel is scored with a rotary diamond saw (not shown) on its outer surface along a line of intersection 20 with an imaginary plane perpendicular to the longitudinal axis of the vessel (FIG. 2). One end 22 0f the scored vessel is then held securely in a vise or similar tool while a force perpendicular to the axis thereof is exerted on the opposite end 23, causing the vessel to snap cleanly along the scored line. At that point, the ambient air rushes into the opening to eliminate the vacuum, and thereby forces any loose particles from the fiber core or the interior of the vessel into the lower-end 22 of the vessel, where such particles will be retained. This assures that these radioactive contaminants will not readily enter the surrounding environment.

By virtue of the core configuration and the surrounding quartz vessel, methods according to the present invention are capable of producing radioactive sources for interstitial, intraluminal or intracavitary brachytherapy, in an iridium fiber core size of 0.343 mm diameter by one mm long, for example, and a core weight of 20 mg, with radioactive dosages of up to 11 curies.

Figure 3:
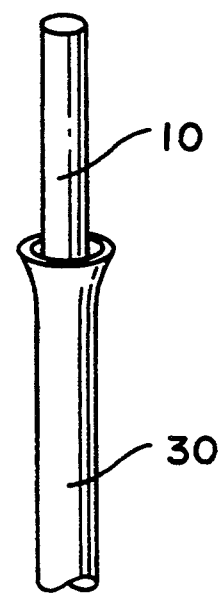
FIG. 3 is a perspective view of the radioactive fiber core being assembled into a source wire.

The radioactive Ir-192 core 10 is subsequently loaded into the slightly flared housing tube 30 of a source wire (FIG. 3), for example, in the manner described in copending U.S. patent application Ser. No. 07/603,471 of the applicant herein, assigned to the same assignee as the present application.

Although a preferred embodiment and method of the present invention has been described herein, it will be apparent from the foregoing description to those skilled in the field of the invention that variations and modifications of the invention may be implemented without departing from the spirit and scope of the invention. For example, core materials other than iridium may be used, with concomitant changes in the size and weight of the final source. Accordingly, it is intended that the invention shall be limited only to the extent required by the appended claims and the rules and principles of applicable law.

What is claimed is:

1. A method of fabricating a radioactive core for a source wire to be used in radiation treatment of tissue at a preselected site within the body of a patient, comprising the steps of:
   providing a thin elongate fiber of a substantially pure source material to be irradiated to an activity level of at least approximately ten curies,
   encapsulating the fiber in a straight tube substantially transparent to the flux of an irradiating beam, with lengthwise orientation along the axis of the tube, so that the fiber is restrained from curling,
   irradiating the tube and the fiber therein with a beam of radiation directed substantially normal to said axis while rotating the tube about said axis, to render the fiber radioactive to said activity level, and
   subsequently removing the fiber from the tube for use as the radioactive core to be installed in a source wire.

2. The method of claim 1, including:
   sealing said fiber within said tube under vacuum before irradiating the tube and the fiber.

3. The method of claim 2, including:
   using a relatively thin walled vessel as said tube, and
   vacuum sealing said fiber within the tube while applying heat, and using heat sinks including the thin-walled tube to transfer, reduce and remove the quantity of heat delivered to the fiber during the vacuum sealing process.

4. The method of claim 1, including:
   using a vessel with a relatively thin wall as said tube to allow substantially unimpeded passage of said beam therethrough.

5. The method of claim 4, including:
   using a vessel composed of substantially pure quartz as said tube to avoid impeding passage of the irradiating beam therethrough and further to avoid contaminating the fiber during irradiation.

6. The method of claim 5, including:
   vacuum sealing said fiber within said tube before irradiating the tube and the fiber.

7. The method of claim 1, including:
   using a vessel composed of substantially pure quartz as said tube to avoid impeding passage of the irradiating beam therethrough and further to avoid contaminating the fiber during irradiation.

8. The method of claim 7, including:
   vacuum sealing said fiber within said tube before irradiating the tube and the fiber.

9. The method of claim 6, including:
   using as said fiber a material selected from the group consisting of iridium, cobalt, cesium, palladium, gold, and iodine, to aid in achieving desired activity level and half life from irradiation.

10. The method of claim 6, including:
    using as said fiber an elongate, cylinder composed of substantially pure iridium having a thickness of approximately 0.35 mm, a length of approximately one cm, and a weight in the range of approximately 20 to 21 mg, to aid in achieving desired activity level and half life from irradiation.

11. The method of claim 10, including:
    irradiating said iridium fiber to a radioactivity level of at least 10 curies.

12. The method of claim 1, including:
    scoring the tube on its outer surface about said axis to allow the tube to be broken cleanly to expose the irradiated fiber for removal thereof.

* * * * *